(12) United States Patent
Norman

(10) Patent No.: US 6,635,067 B2
(45) Date of Patent: Oct. 21, 2003

(54) LIQUID COOLED, POWERED SURGICAL HANDPIECE

(75) Inventor: Gerould W. Norman, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 100 days.

(21) Appl. No.: 09/956,301

(22) Filed: Sep. 19, 2001

(65) Prior Publication Data

US 2002/0040229 A1 Apr. 4, 2002

Related U.S. Application Data

(60) Provisional application No. 60/235,213, filed on Sep. 24, 2000.

(51) Int. Cl.[7] .............................................. A61B 19/00
(52) U.S. Cl. .......................... 606/180; 606/22; 606/80
(58) Field of Search ............................... 606/1, 22, 23, 606/79, 80, 167, 180; 433/82, 104, 114; 408/57; 451/488; 30/123.3; 83/170, 171; 310/54, 58, 64, 65

(56) References Cited

U.S. PATENT DOCUMENTS

| | | |
|---|---|---|
| 2,363,141 A | 11/1944 | Pertics |
| 2,453,349 A | 11/1948 | Stalder |
| 2,473,583 A | 6/1949 | Grögol |
| 3,324,552 A | 6/1967 | Saffir |
| 3,604,960 A | 9/1971 | Krestel |
| 4,007,529 A * | 2/1977 | Fleer .................. 433/104 |
| 4,184,256 A * | 1/1980 | Loge et al. ............. 433/82 |
| 4,217,101 A * | 8/1980 | Loge .................. 433/126 |
| 4,802,852 A | 2/1989 | Shea |
| 5,165,503 A * | 11/1992 | Hoffman ............... 184/55.1 |
| 5,910,152 A | 6/1999 | Bays |
| 6,050,989 A | 4/2000 | Fox et al. |

FOREIGN PATENT DOCUMENTS

DE 31 36 880 A1 7/1983

OTHER PUBLICATIONS

XoMed Brochure, "The Straightshot® Magnum", 2 pgs.; Aug. 1998.
Webpage relating to Hall Surgical/Linuatec's E9000 Drill, 1 pg.
Copy of PCT Search Report mailed Apr. 9, 2002 (6 pgs.).

* cited by examiner

Primary Examiner—Eduardo C. Robert
Assistant Examiner—David C. Comstock
(74) Attorney, Agent, or Firm—Curtis Kinghorn; Timothy A. Czaja

(57) ABSTRACT

A powered surgical handpiece for use with a micro-cutting instrument, includes a motor contained within a housing. The housing includes a motor enclosure surrounding the motor and a sleeve placed about the motor enclosure. An internal passage is formed entirely between the sleeve and the motor enclosure. Finally, the sleeve defines a handling region and forms inlet and outlet ports proximal the handling region which are fluidly connected to the internal passage. During use, a cooling fluid, flows through the internal passage as the cooling fluid circulates from the inlet port to the outlet port. The motor is sealed relative to the cooling fluid by the motor enclosure. Thus, the cooling fluid does not directly contact the motor, but instead serves as a heat exchange medium through which heat generated by the motor is thermally transferred to the cooling fluid via the motor enclosure.

28 Claims, 4 Drawing Sheets

LIQUID COOLED, POWERED SURGICAL HANDPIECE

CROSS-REFERENCE TO RELATED APPLICATIONS

This application claims the benefit of U.S. Provisional Application Serial No. 60/235,213, filed on Sep. 24, 2000, the teachings of which are incorporated herein by reference.

BACKGROUND OF THE INVENTION

The present invention relates to a powered handpiece for driving surgical blades. More particularly, it relates to a liquid cooled, powered surgical handpiece for use in driving a surgical blade assembly, such as a surgical drill.

Powered handpieces are commonly used in many medical specialties to drive surgical blades for performing various diverse cutting functions including resection, dissection, debridement, shaving, drilling, pulverizing, and shaping of anatomical tissue. In the areas of ENT/head/neck surgery, powered or motorized handpieces and systems are commonly connected to a surgical cutting instrument including an outer tubular member forming a cutting window at a distal end thereof, and an inner blade member coaxially disposed within the outer tubular member. The inner blade assembly terminates at a distal cutting tip. With this configuration, the powered handpiece rotates and/or oscillates the inner blade member relative to the outer tubular member so as to cause the distal cutting tip to perform a desired cutting operation. Alternatively, a more conventional micro-drill bit having a cutting tip can also be connected to, and be driven by, the powered handpiece. Regardless, because the cutting procedures associated with ENT/head/neck surgery are highly delicate, yet require numerous cutting motions or rotations by the cutting tip to complete the procedure, the powered handpiece greatly decreases procedure time requirements and the physical drain on the surgeon.

Undoubtedly, surgical powered handpieces used in combination with micro-cutting instruments are highly beneficial. As with any motor, however, operation of a powered handpiece generates heat. This is especially true for ENT/head/neck procedures where the motor associated with the surgical handpiece is required to operate at highly elevated speeds. Because the surgeon directly handles the powered handpiece, over time the generated heat can cause distinct hand discomfort. This is especially true during prolonged procedures. Obviously, any distractions may negatively affect the surgeon's performance.

Powered surgical handpieces continue to be highly useful with surgical micro-cutting instruments, especially bone drilling instruments. However, the heat generated by the powered handpiece can lead to user discomfort and may limit usefulness of the device. Therefore, a need exists for a powered surgical handpiece incorporating a cooling system.

SUMMARY OF THE INVENTION

One aspect of the present invention provides a powered surgical handpiece for use with a micro-cutting instrument, especially a bone-drilling device useful for ENT/head/neck procedures. The powered surgical handpiece includes a motor contained within a housing. The housing includes a motor enclosure surrounding the motor and a sleeve placed about the motor enclosure. At least a portion of the sleeve has an inner diameter greater than an outer diameter of a corresponding portion of the motor enclosure, such that the housing defines an internal gap or passage. Finally, the sleeve forms inlet and outlet ports that are fluidly connected to the internal passage. During use, a cooling fluid, such as de-ionized water or saline, is forced into the internal passage via the inlet port. The motor is sealed relative to the cooling fluid by the motor enclosure. Thus, the cooling fluid does not directly contact the motor, but instead serves as a heat exchange medium through which heat generated by the motor is thermally transferred to the cooling fluid via the motor enclosure. The now heated fluid exits the housing at the outlet port. As a result of the thermal transfer of heat from the motor to the cooling fluid, and the subsequent evacuation of the now-heated fluid away from the handpiece, heat transfer to an outer surface of the housing, otherwise handled by the surgeon, is minimized. In an alternative embodiment, the housing is configured to define a serpentined or specifically routed internal fluid path to optimize heat transfer.

DESCRIPTION OF THE PREFERRED EMBODIMENTS

Figure 1:
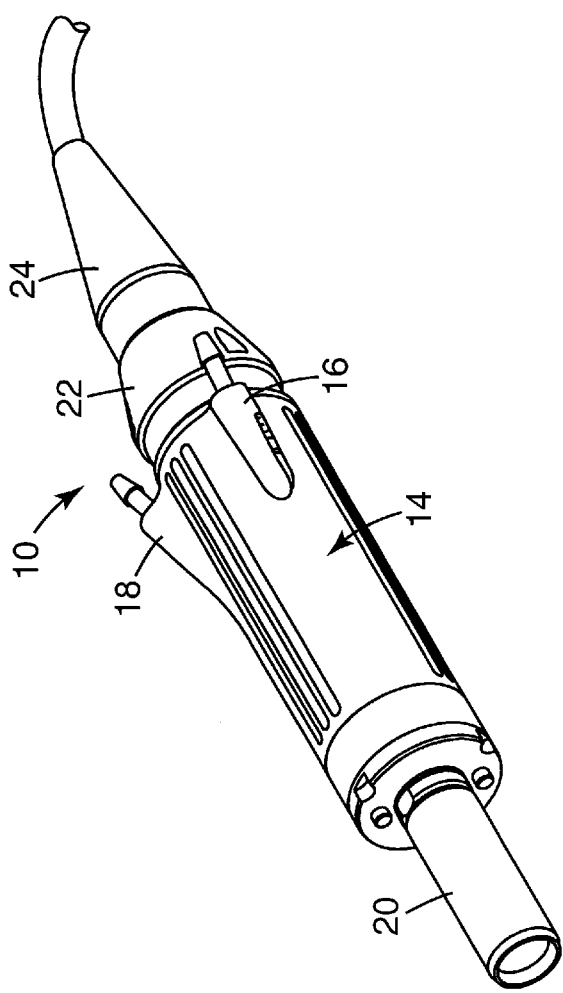
FIG. 1 is a perspective view of a powered surgical handpiece in accordance with the present invention in conjunction with a surgical tool.
Figure 1:
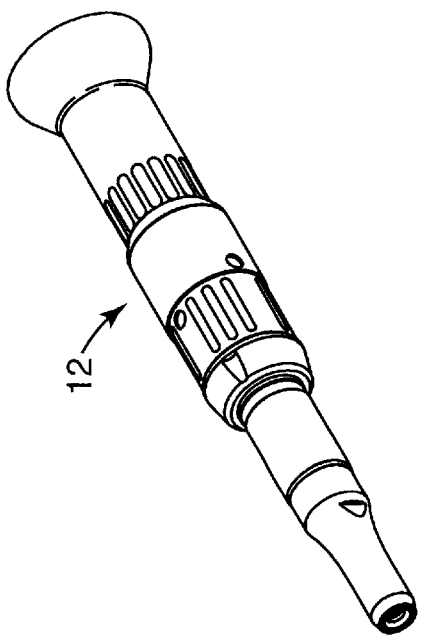

One preferred embodiment of a powered surgical handpiece 10 is shown in conjunction with a surgical cutting tool 12 in FIG. 1. As a point of reference, the surgical cutting tool 12 is depicted in FIG. 1 as being a surgical bone drill useful for ENT/head/neck procedures as is known in the art. Alternatively, a wide variety of other surgical cutting tools can be connected to, and powered by, the powered surgical handpiece 10. For example, the surgical cutting tool 12 can be a micro-resecting instrument, a micro-debriding instrument, a micro-shaving instrument, etc., all of which are well known. Regardless, however, the powered surgical handpiece 10 is particularly adapted to be selectively coupled to surgical cutting tools useful with ENT/head/neck procedures. It should be understood that this concept could also be applied to the powered surgical handpiece 10 with an integral (or permanently coupled) surgical cutting tool.

With the above applications in mind, the powered surgical handpiece 10 includes a housing 14 containing a motor (not shown). As described in greater detail below, the housing 14 forms an inlet port 16 and an outlet port 18 adjacent a distal end thereof. Further, in one preferred embodiment, the handpiece 10 includes a collet 20 surrounding a drive chuck (not shown) otherwise driven by internal components of the motor. As is known in the art, the collet 20 is formed to effectuate coupling between the surgical handpiece 10 and the surgical cutting tool 12. Further, and as described in greater detail below, the handpiece 10 is connected at the distal end 22 to an electrical cord assembly 24 by a connector. The electrical cord assembly 24 is electrically connected to a power source (not shown) and/or power console (not shown) for transmitting electricity to the motor. In the preferred embodiment, the electrical cord is permanently connected, but it should be understood that this could also be a removable connection. Alternatively, where varying power sources are employed (e.g., battery powered), the electrical cord assembly 24 can be eliminated.

Figure 2:
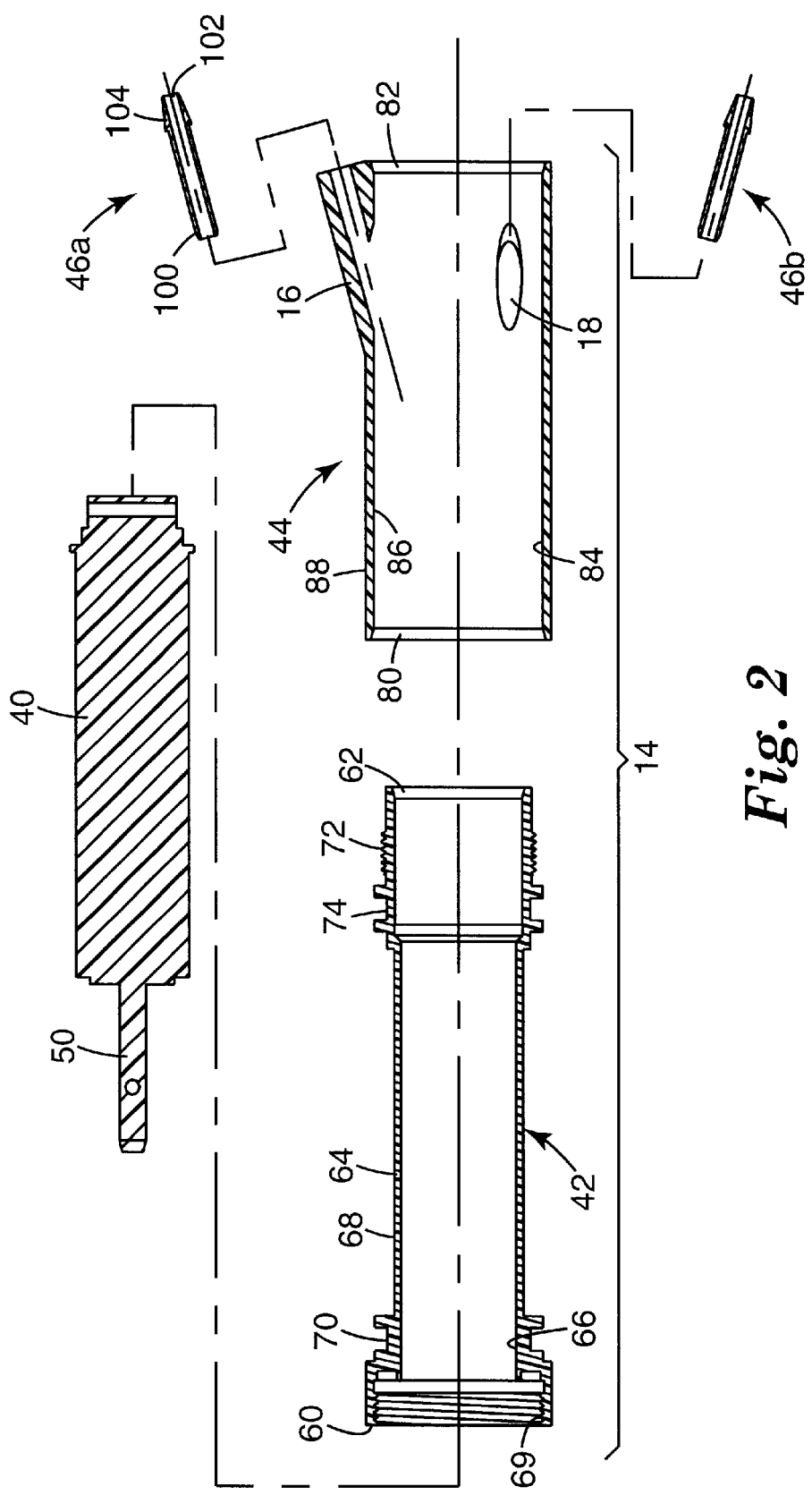
FIG. 2 is an exploded, cross-sectional view of the powered surgical handpiece of FIG. 1.

The powered surgical handpiece 10, including the housing 14 and a motor 40, as shown in greater detail in FIG. 2. The housing 14 includes a motor enclosure 42, a sleeve 44, and port fitments 46a and 46b. As described below, the motor enclosure 42 maintains the motor 40. The sleeve 44 coaxially receives the motor enclosure 42 and defines the inlet port 16 and the outlet port 18. Finally, the port fitments 46a, 46b are connected to the inlet port 16 and the outlet port 18, respectively.

The motor 40 is of a type commonly known in the art, and is preferably a three-phase brushless DC motor. Alternatively, other available motor designs can be incorporated, including, but not limited to, a battery-powered motor, a pneumatic-type motor, etc. Regardless, operation of the motor 40 drives movement of a drive coupling 50 (i.e., rotational, oscillation, etc.), that is otherwise coupled to the surgical cutting device 12 (FIG. 1).

The motor enclosure 42 is an elongated, tubular body having a leading end 60, a trailing end 62, an intermediate section 64, a central passage 66, and an outer surface 68 along the intermediate section 64. The motor enclosure 42 is sized and shaped in accordance with the motor 40 such that the motor enclosure 42 has a length approximating a length of the motor 40 and an inner diameter or dimension approximating an outer diameter or dimension of the motor 40. Thus, in one preferred embodiment, the motor enclosure 42 has a length of approximately 2.85 inches, and an inner diameter along the intermediate section 64 of approximately 0.512 inch. With this one preferred embodiment, the outer surface 68 of the intermediate section 64 has a preferred diameter or dimension of 0.572 inch. Obviously, these dimensions can vary depending upon a size and construction of the motor 40 so long as the motor enclosure 42 is configured to be in relatively direct contact with the motor 40 along a majority of at least the intermediate section 64. In addition, while the motor 40 has been depicted in FIG. 2 as being cylindrical (i.e., circular in transverse cross-section), other shapes are equally acceptable (e.g., square, octagonal, etc., in transverse cross-section), it being understood that a shape of at least an inner surface of the intermediate section 64 corresponds with a shape of the so-provided motor 40. Further, the motor 40 is typically provided with a separate housing about which the motor enclosure 42 is assembled. To facilitate coupling of the motor enclosure 42 to other components, the leading end 60 preferably forms an internally threaded flange 69 and a leading O-ring groove 70. Similarly, the trailing end 62 forms an externally threaded flange 72 and a trailing O-ring groove 74. Alternatively, other coupling configurations can be employed. Regardless, the motor enclosure 42 is formed from a rigid, thermally conductive material, preferably 303 stainless steel.

The sleeve 44 is an elongated, tubular body, defining a leading end 80, a trailing end 82 and a central passage 84. The central passage 84 is defined by an inner surface 86. The inlet port 16 and the outlet port 18 are further formed by the sleeve 44 and are fluidly connected to the central passage 84. In this regard, the ports 16, 18 are formed adjacent the trailing end 82, preferably extending in a rearward fashion (relative to the orientation of FIG. 2). In this regard, the sleeve 44 includes a handling region 88 defined along an outer surface thereof. As shown in FIG. 2, the ports 16, 18 are preferably disposed between the handling region 88 and the trailing end 82, and extend away (rearwardly) from the handling region 88. The handling region 88 is configured for convenient grasping by a surgeon. As described below, by preferably positioning and orienting the ports 16, 18 behind and away from the handling region 88, the inlet ports 16, 18 and other components (otherwise attached to the ports 16, 18) will not impede the surgeon's grasping of the handpiece 10 along the handling region 88.

The sleeve 44 is sized and shaped in accordance with the motor enclosure 42, and thus preferably corresponds generally with a size and shape of the motor 40. With respect to the previously described preferred embodiment of the motor enclosure 42 in which the outer surface 68 of the intermediate section 64 has an outer diameter or dimension of approximately 0.572 inch, the inner surface 86 of the sleeve 44 preferably defines an inner diameter or dimension of approximately 0.75 inch. As described below, by forming the sleeve 44 to have an inner diameter or dimension greater than an outer diameter or dimension of the motor enclosure 42, relative to at least the intermediate section 64, a spacing is established between the two components upon final assembly. The sleeve 44 is preferably formed from a rigid, machinable material, preferably 303 stainless steel.

The port fitments 46a, 46b are configured for engagement within the respective ports 16, 18 formed by the sleeve 44. In this regard, each of the port fitments 46a, 46b are tubular bodies having a leading end 100 and a trailing end 102. In a preferred embodiment, the trailing end 102 forms a conical flange 104 configured to frictionally receive an external component, such as flexible tubing. Regardless, in a preferred embodiment, the port fitments 46a, 46b are formed of a rigid material, preferably 17-4 stainless steel.

Figure 3:
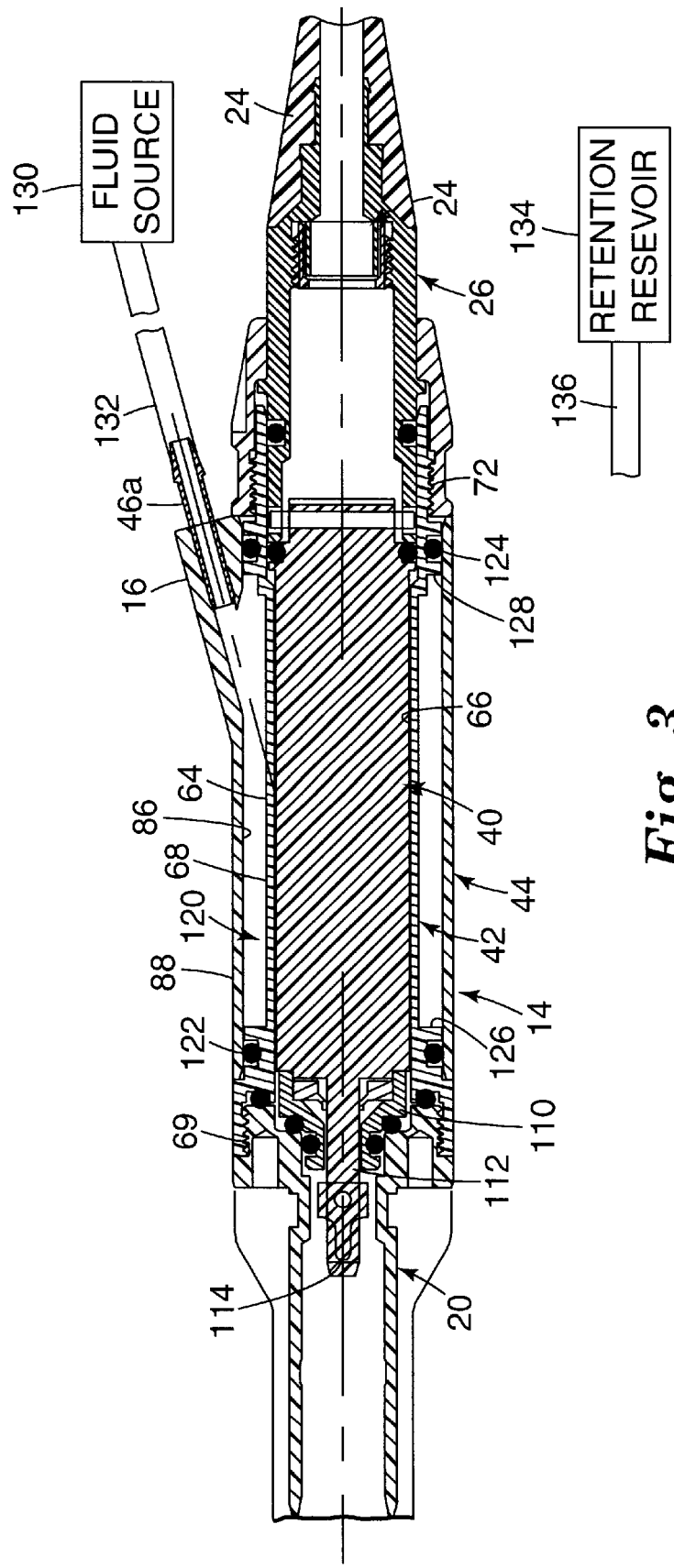
FIG. 3 is an enlarged, cross-sectional view of the powered surgical handpiece of FIG. 1 upon final assembly.

Assembly and operation of the powered surgical handpiece 10 is best described with reference to FIG. 3. The motor 40 is positioned within the central passage 66 of the motor enclosure 42. The motor enclosure 42, in turn, is disposed within the sleeve 44. Finally, the port fitments 46a, 46b are secured to the inlet port 16 and the outlet port 18, respectively.

Depending upon the particular surgical application, additional components can be assembled to the surgical handpiece 10. For example, the collet 20 can be coupled to the handpiece 10 via the internally threaded flange 69 of the motor enclosure 42. In the one preferred embodiment, the collet 20 maintains a support piece 110 relative to the motor 40. The support piece 110 supports a drive shaft 112 otherwise maintaining the drive chuck 114. Similarly, FIG. 3 illustrates the connector 26 coupling the electrical cord assembly 24 to the surgical handpiece 10 via the externally threaded flange 72 of the motor enclosure 42.

Regardless of whether other components, such as the collet 20, the electrical cord assembly 24, and the connector 26, are mounted to the surgical handpiece 10, a gap or internal passage (or passage) 120 is defined between the inner surface 86 of the sleeve 44 and the outer surface 68 of the intermediate section 64 of the motor enclosure 42. The internal passage 120 is fluidly connected to the inlet port 16 and the outlet port 18 (FIG. 1), and thus to the respective port fitments 46a, 46b. The internal passage 120 preferably extends from a first end 126 along a majority of the longitudinal length of the motor enclosure 42, and thus the motor 40, to a second end 128. Further, in one preferred embodiment, the internal passage 120 uniformly encompasses a circumference (or the outer surface 68) of the motor enclosure 42, and thus of the motor 40, it being recalled that the motor 40 and/or the motor enclosure can assume shapes other than cylindrical. To prevent fluid egress other than through the outlet port, the first and second ends 126, 128 of the internal passage are more completely sealed by use of first and second O-rings 122, 124. The first O-ring 122 is disposed within the leading O-ring groove 70 of the motor enclosure 42, and sealingly engages a corresponding portion of the sleeve 44. Similarly, the second O-ring 124 is disposed within the trailing O-ring groove 74 of the motor enclosure 42, again sealingly engaging a corresponding portion of the sleeve 44.

During use, a continuous supply of a cooling liquid (e.g., de-ionized water, saline, etc.) is forced into the internal passage 120 via the inlet port 16. For example, a fluid source 130 (shown generally in FIG. 3) is fluidly connected to the port fitment 46a otherwise secured within the inlet port 16. For example, a flexible tube or hose 132 fluidly connects the fluid source 130 to the port fitment 46a. The fluid source 130 can include a fluid pump (not shown) that continuously forces the cooling fluid into the housing 14. Alternatively, the fluid source 130 can be positioned to gravity feed the cooling fluid to the housing 14.

Conversely, the outlet port 18 (FIG. 1) is fluidly connected to a retention reservoir 134 (shown generally in FIG. 3) via tubing 136 otherwise fluidly connected to the port fitment 46b (FIG. 2). Cooling fluid forced into the inlet port 16 is directed by the internal passage 120 along the outer surface 68 of the motor enclosure 42. Heat generated by operation of the motor 40 is transferred through the motor enclosure 42 to the cooling fluid at the outer surface 68. The continuous supply of the cooling fluid through the inlet port 16 directs the now heated liquid from the internal passage 120, and thus the housing 14, via the outlet port 18, where it is subsequently collected in the retention reservoir 134. Although not illustrated in FIG. 3, in a preferred embodiment, the fluid otherwise exiting the housing 14 via the outlet port 18 is preferably recirculated or returned to the fluid source 130. Thus, the outlet port 18 can be directly connected to the fluid source 130, or the retention reservoir 134 can be fluidly connected to the fluid source 130. Alternatively, the exiting fluid need not be recirculated, and can instead be collected in the retention reservoir 134.

The cooling fluid removes heat otherwise generated by the motor 40 through thermal conduction (laminar flow) as the cooling fluid passes through the internal passage 120. As a result, little, if any, heat generated by the motor 40 is transferred to the sleeve 44, and in particular the handling region 88. A surgeon otherwise operating the powered surgical handpiece 10 by grasping the handling region 88 will experience minimal hand discomfort. Further, the ports 16, 18 are positioned and orientated so as to not obstruct the surgeon's efforts when using the handpiece 10. That is to say, the ports 16, 18, and the associated tubing 132, 136, are positioned and extend rearward relative to the handling region 88, and so are out of the way of the surgeon's hand(s). Additionally, by providing the motor enclosure 42 as a component separate from the motor 40, the motor 40 itself remains dry (i.e., is protected by the motor enclosure 42 from the cooling fluid).

Figure 4:
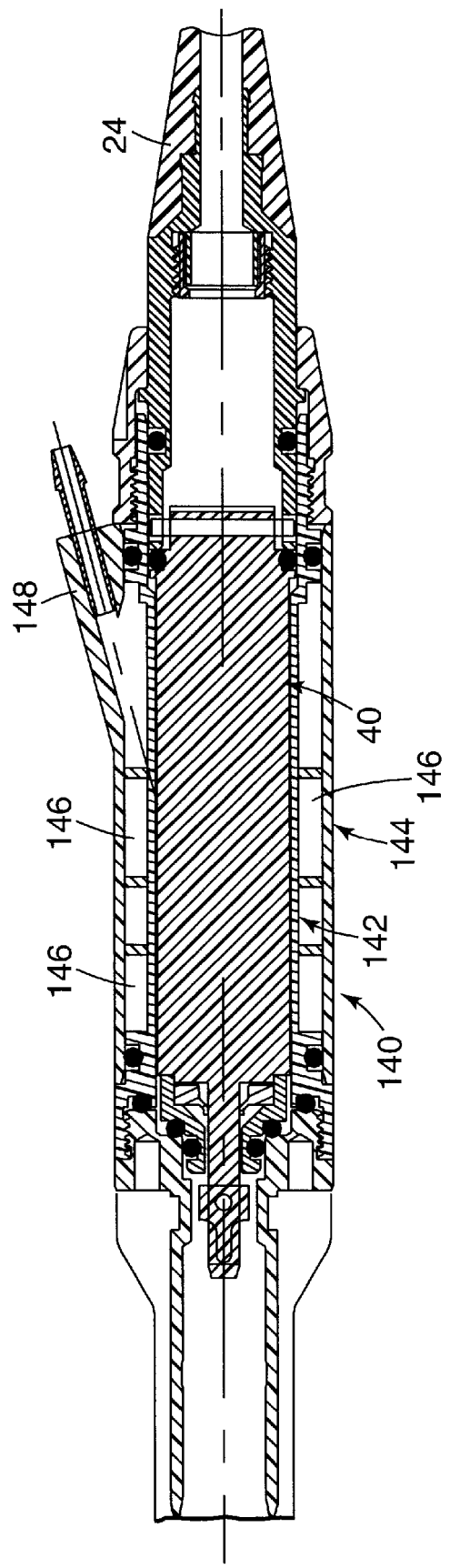
FIG. 4 is an enlarged, cross-sectional view of an alternative embodiment powered surgical handpiece in accordance with the present invention.

While the internal passage 120 has been preferably described as uniformly encompassing an entire circumference (or the outer surface 68) of the motor enclosure 42, and thus the motor 40, alternative configurations are also available. For example, FIG. 4 illustrates an alternative housing 140 including a motor enclosure 142 and a sleeve 144 defining an internal passage 146 therebetween. The motor enclosure 142 and/or the sleeve 144 are configured such that the internal passage 146 has a serpentined configuration as it extends from an inlet port 148 to an outlet port (not shown). Even further, the gap 146 can be routed over a more specific path relative to the motor 40 to optimize heat removal.

The powered surgical handpiece of the present invention provides a marked improvement over previous designs. In particular, the powered surgical handpiece incorporates a unique housing that directs a cooling liquid across the motor, thereby minimizing surgeon hand discomfort due to motor-generated heat. Further, the surgical handpiece does not obstruct the surgeon's use thereof, and is particularly useful for ENT/head/neck cutting tools and surgical bone drills.

What is claimed is:

1. A powered surgical handpiece for use with a micro-cutting instrument, the handpiece comprising:
   a housing comprising:
      a sleeve defining a handling region and forming an inlet port and an outlet port proximal the handling region,
      a motor enclosure maintained within the sleeve, the motor enclosure defining an intermediate section,
      an internal passage formed entirely between the sleeve and the motor enclosure, and
      wherein the inlet port and the outlet port are fluidly connected to the internal passage, and the internal passage is configured to allow a cooling fluid to circulate from the inlet port to the outlet port; and
   a motor maintained within the motor enclosure, wherein the internal passage and the motor are similarly located along the intermediate section;
   wherein the handpiece is configured to provide mechanical power and be selectively coupled to a micro-cutting instrument.

2. The powered surgical handpiece of claim 1, wherein the handling region is configured to be grasped by an instrument operator.

3. The powered surgical handpiece of claim 1, wherein the motor enclosure defines an inner surface, the motor defines an outer surface, and further wherein the inner surface is in substantially direct contact with the outer surface.

4. The powered surgical handpiece of claim 1, wherein the motor enclosure is sealed about the motor to prevent contact between the motor and the cooling fluid.

5. The powered surgical handpiece of claim 1, wherein the internal passage has a length approximating a length of the motor.

6. The powered surgical handpiece of claim 1, wherein the internal passage has a first end and a second end, further wherein the first end and the second are sealed.

7. The powered surgical handpiece of claim 1, wherein the internal passage uniformly encompasses a perimeter of the intermediate section of the motor enclosure.

8. The powered surgical handpiece of claim 1, wherein the internal passage is routed over a serpentine path relative to the motor.

9. The powered surgical handpiece of claim 1, wherein the inlet is positioned proximate to the motor.

10. The powered surgical handpiece of claim 1, wherein the inlet port is fluidly connected to a fluid pump, the fluid pump being configured to continuously force cooling fluid into the internal passage.

11. The powered surgical handpiece of claim 10, wherein the outlet port is fluidly connected to a retention reservoir.

12. The powered surgical handpiece of claim 11, wherein the fluid pump and the retention reservoir are both components of a recirculated cooling fluid source.

13. A powered micro-cutting instrument assembly comprising:
   a micro-cutting instrument; and a handpiece configured to be selectively coupled to the micro-cutting instrument, the handpiece comprising:
  a sleeve defining a handling region and forming an inlet port and an outlet port proximal the handling region,
  a motor enclosure maintained within the sleeve, the motor enclosure defining an intermediate section,
  an internal passage formed entirely between the sleeve and the motor enclosure, wherein the inlet port and the outlet port are fluidly connected to the internal passage, and
  a motor maintained within the motor enclosure, the motor being configured to provide mechanical power to the micro-cutting instrument,
  wherein the internal passage and the motor are similarly located along the intermediate section; and
a cooling fluid circulated through the internal passage from the inlet port to the outlet port; wherein such circulation reduces the heat transfer from the motor to the sleeve.

14. The assembly of claim 13, wherein the handling region is configured to be grasped by an instrument operator.

15. The assembly of claim 13, wherein the motor enclosure forms an inner surface, the motor forms an outer surface, and further wherein the inner surface is in substantially direct contact with the outer surface.

16. The assembly of claim 13, wherein the motor enclosure is sealed about the motor to prevent contact between the motor and the cooling fluid.

17. The assembly of claim 13, wherein the internal passage has a length approximating the length of the motor.

18. The assembly of claim 13, wherein the internal passage has a first end and a second end, further wherein the first end and the second are sealed.

19. The assembly of claim 13, wherein the internal passage uniformly encompasses a perimeter of the intermediate section of the motor enclosure.

20. The assembly of claim 13, wherein the internal passage is routed over a serpentine path relative the motor.

21. The assembly of claim 13, wherein the inlet port is positioned proximate to the motor.

22. The assembly of claim 13, wherein the inlet port is fluidly connected to a fluid pump, the fluid pump being configured to continuously force cooling fluid into the internal passage.

23. The assembly of claim 22, wherein the outlet port is fluidly connected to a retention reservoir.

24. The assembly of claim 23, wherein the fluid pump and the retention reservoir are both components of a recirculated cooling fluid source.

25. A method of cooling a powered surgical handpiece configured for use with a micro-cutting instrument, the method comprising:
  providing the handpiece comprising:
    a housing forming an internal passage entirely between a sleeve and a motor enclosure, wherein the sleeve forms an inlet port and an outlet port, each port being fluidly connected to the internal passage, and
    a motor maintained within the motor enclosure, wherein the motor and the internal passage are similarly located along the motor enclosure; and
  providing a fluid source;
  fluidly connecting the fluid source to the inlet port;
  providing a retention reservoir configured to collect a cooling fluid;
  fluidly connecting the outlet port to the retention reservoir;
  coupling the handpiece to a surgical micro-cutting instrument;
  operating the micro-cutting instrument in a surgical area by powering the handpiece;
  operating the fluid source to continuously circulate cooling fluid through the inlet port directly to the internal passage and subsequently through the outlet port to the retention reservoir while not discharging fluid to the surgical area, wherein heat generated by the motor is transferred through the motor enclosure to the cooling fluid to reduce heat transfer to the sleeve.

26. The method of claim 25, further comprising:
  recirculating cooling fluid from the retention reservoir to the fluid source.

27. The method of claim 25, wherein operating the fluid source includes preventing cooling fluid from contacting the motor.

28. The method of claim 25, wherein providing the handpiece includes providing the internal passage with a first end and a second end, the first and the second end being sealed.

* * * * *